United States Patent
Pikus et al.

(10) Patent No.: US 8,740,936 B2
(45) Date of Patent: Jun. 3, 2014

(54) PINCH VASCULAR CLOSURE APPARATUS AND METHOD

(75) Inventors: Michael Pikus, Golden Valley, MN (US); Patrick Haverkost, Brooklyn Center, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 74 days.

(21) Appl. No.: 13/218,169

(22) Filed: Aug. 25, 2011

(65) Prior Publication Data

US 2012/0065669 A1 Mar. 15, 2012

Related U.S. Application Data

(60) Provisional application No. 61/382,153, filed on Sep. 13, 2010.

(51) Int. Cl.
*A61B 17/03* (2006.01)
(52) U.S. Cl.
USPC ............ 606/216; 606/215; 606/157; 606/158
(58) Field of Classification Search
USPC ................................................. 606/215, 216
See application file for complete search history.

(56) References Cited

U.S. PATENT DOCUMENTS

| | | | |
|---|---|---|---|
| 5,782,861 A | 7/1998 | Cragg et al. | |
| 5,964,782 A | 10/1999 | Lafontaine et al. | |
| 6,063,085 A * | 5/2000 | Tay et al. | 606/50 |
| 6,676,685 B2 * | 1/2004 | Pedros et al. | 606/213 |
| 6,719,777 B2 | 4/2004 | Ginn et al. | |
| 6,749,622 B2 | 6/2004 | McGuckin, Jr. et al. | |
| 7,211,101 B2 | 5/2007 | Carley et al. | |
| 7,326,230 B2 | 2/2008 | Ravikumar | |
| 7,722,641 B2 * | 5/2010 | van der Burg et al. | 606/216 |
| 7,819,895 B2 | 10/2010 | Ginn et al. | |
| 7,875,043 B1 | 1/2011 | Ashby et al. | |
| 7,901,428 B2 | 3/2011 | Ginn et al. | |
| 7,931,669 B2 | 4/2011 | Ginn et al. | |
| 7,942,897 B2 | 5/2011 | Lafontaine | |
| 8,114,123 B2 * | 2/2012 | Brenzel et al. | 606/213 |
| 2004/0122349 A1 | 6/2004 | Lafontaine et al. | |
| 2005/0010248 A1 | 1/2005 | Lafontaine | |
| 2006/0167485 A1 | 7/2006 | Blatter | |
| 2007/0049967 A1 | 3/2007 | Sibbitt, Jr. et al. | |
| 2007/0049968 A1 | 3/2007 | Sibbitt, Jr. et al. | |
| 2007/0060895 A1 | 3/2007 | Sibbitt, Jr. et al. | |
| 2008/0065152 A1 * | 3/2008 | Carley | 606/215 |
| 2009/0088794 A1 * | 4/2009 | LaFontaine | 606/213 |
| 2009/0177212 A1 | 7/2009 | Carley et al. | |
| 2009/0254119 A1 | 10/2009 | Sibbitt, Jr. et al. | |
| 2010/0130965 A1 * | 5/2010 | Sibbitt et al. | 606/2 |
| 2010/0234884 A1 | 9/2010 | Lafontaine et al. | |
| 2011/0218568 A1 | 9/2011 | Voss | |
| 2012/0179172 A1 * | 7/2012 | Paul et al. | 606/142 |

* cited by examiner

*Primary Examiner* — Melanie Tyson
*Assistant Examiner* — Todd J Scherbel
(74) *Attorney, Agent, or Firm* — Seager, Tufte & Wickhem, LLC

(57) ABSTRACT

A device for pinching an opening in a vessel wall, comprising an introducer sheath, a lumen having a distal opening and a bleed hole; an anchoring having a cylindrical shape in a first constrained state and a flared shape in a second unconstrained state; a pincher member slidably disposed between the anchoring member and the introducer sheath comprising at its distal end a plurality of elongate pincher arms, each of the plurality of elongate pincher arms having a free distal end such that when the pincher member distal end is unconstrained, the free distal ends of the elongate pincher arms are biased to expand radially; and an interior support member slidably disposed in the anchoring member comprising a plurality of elongate support legs, each having a free distal end such that when the distal end of the interior support member is unconstrained, the free distal ends curve outwardly.

9 Claims, 9 Drawing Sheets

PINCH VASCULAR CLOSURE APPARATUS AND METHOD

RELATED APPLICATIONS

This application claims priority to U.S. Ser. No. 61/382,153 filed Sep. 13, 2010.

FIELD

The present disclosure relates generally to medical devices and more particularly to methods and devices for closing and/or sealing punctures in tissue.

BACKGROUND

In many medical procedures, such as, for example, balloon angioplasty and the like, an opening can be created in a blood vessel or arteriotomy to allow for the insertion of various medical devices which can be navigated through the blood vessel to the site to be treated. For example, a guidewire may first be inserted through the tissue tract created between the skin, or the epidermis, of the patient down through the subcutaneous tissue and into the opening formed in the blood vessel. The guidewire may then be navigated through the blood vessel to the site of the occlusion or other treatment site. Once the guidewire is in place, an introducer sheath can be slid over the guide wire to form a wider, more easily accessible, tract between the epidermis and the opening into the blood vessel. The appropriate medical device can then be introduced over the guidewire through the introducer sheath and then up the blood vessel to the site of the occlusion or other treatment site.

Once the procedure is completed, the medical devices or other equipment introduced into the vessel can be retracted through the blood vessel, out the opening in the blood vessel wall, and out through the tissue tract to be removed from the body. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. However, there is an ongoing need to provide new and improved device structures, assemblies, and/or methods for closing and/or sealing the opening in the blood vessel and/or tissue tract.

BRIEF SUMMARY

An embodiment of the present disclosure is a device for sealing an opening in a vessel wall. The device may have an introducer sheath having a proximal end, a distal end, a longitudinal axis extending between the proximal and distal ends, a lumen having an opening at the distal end and a bleed hole proximate the distal end. The device also may have an anchoring member having a tubular shape and an interior lumen having an opening at a distal end of the anchoring member may be slidably disposed in the introducer sheath. The distal end of the anchoring member may have a cylindrical shape in a first constrained state and a flared shape in a second unconstrained state. The device also may have a pincher member that may be slidably disposed between the anchoring member and the introducer sheath. The pincher member, having a proximal end and a distal end, may include at its distal end a plurality of elongate pincher arms, where each of the plurality of elongate pincher arms may have a free distal end such that when the pincher member distal end is unconstrained by the introducer sheath, the free distal ends of the elongate pincher arms are biased to expand radial away from the anchoring member. The device may include an interior support member slidably disposed in the anchoring member. The interior support member, having a proximal end and a distal end, may comprise at its distal end a plurality of elongate support legs, where each of the plurality of elongate support legs may have a free distal end such that when the distal end of the interior support member is unconstrained, the free distal ends of the plurality of elongate support legs curve outwardly away from the longitudinal axis.

In some embodiments, the anchoring member may comprise a plurality of resilient wires that extend parallel to the longitudinal axis when in the constrained state or are woven in a loose weave. The distal ends of the elongate pincher arms may have sharp distal points. When the distal end of the interior support member is unconstrained, the free distal ends of the plurality of elongate support legs may point in a proximal direction.

Another embodiment of the present disclosure pertains to a method for pinching an opening in a vessel wall closed that may include the following illustrative steps. A guidewire may be introduced percutaneously into a blood vessel having a vessel wall. Such a guidewire may ordinarily be introduced prior to starting the method of pinching closed an opening in a vessel wall. For example, the guidewire may be introduced for a prior therapeutic procedure such as an angioplasty procedure. The method for pinching may begin by introducing an introducer sheath having a distal end and a bleed hole near the distal end. The introducer sheath may be advanced over the guidewire until the bleed hole is distal the vessel wall. Once the introducer sheath is in place, an anchoring mechanism having a distal end that expands when unconstrained may be advanced out through the distal end of the introducer sheath until the distal end of the anchoring mechanism is distal the distal end of the introducer sheath. At this point, the anchoring member distal end is free to expand. After the anchoring member distal end expands, the introducer sheath and anchoring mechanism may be moved proximally until the expanded distal end of the anchoring mechanism abuts the vessel wall. The device for the method includes a pincher member having a proximal end and a distal end, and including at its distal end a plurality of elongate pincher arms. Each of the plurality of elongate pincher arms may have a free distal end such that when the pincher member distal end is unconstrained, the free distal ends of the elongate pincher arms are biased to expand radially. The pincher member may be positioned such that the distal end of the pincher member is inside the introducer sheath and proximate the vessel wall. The introducer sheath may then be retracted relative to the pincher member such that the plurality of elongate pincher arm distal ends expand radially. At which point, the pincher member may then be advanced such that the distal ends of the elongate pincher arms engage the vessel wall. The introducer sheath may then be advanced over the pincher member to collapse the distal ends of the plurality of elongate pincher arms. This causes the opening in the vessel wall to be pinched closed. Prior to withdrawing the device, the doctor waits a period of time to allow clotting or hemostasis to occur at the opening. The anchoring member, pincher member and the introducer sheath may be withdrawn proximally.

The method may also include the steps of introducing an interior support member slidably disposed in the anchoring member, the interior support member having a proximal end and a distal end, the interior support member comprising at its distal end a plurality of elongate support legs, each of the plurality of elongate support legs having a free distal end such that when the distal end of the interior support member is unconstrained, the free distal ends of the plurality of elongate support legs curve outwardly away from the longitudinal axis. The interior support member may be advanced distally out from the anchoring member to provide support to interior of the vessel wall with the interior support member.

The elements of the apparatus used in the method may include any of the features described above with respect to the apparatus embodiment. The distal end of the anchoring mechanism may expand to create a proximally facing surface that abuts the vessel wall. The period of time sufficient to permit clotting may be between 5 and 10 minutes. Advancing the introducer sheath over the pincher member to collapse the distal ends of the plurality of elongate pincher arms may cause the opening in the vessel wall to contract in size or close. When the distal ends of the elongate pincher arms engage the vessel wall, the distal ends of the elongate support legs may pierce the vessel wall. The anchoring member and the support member may be withdrawn prior to withdrawing the pinching member and may be withdrawn prior to waiting for the period of time.

BRIEF DESCRIPTION OF THE DRAWINGS

Embodiments of the present disclosure may be more completely understood in consideration of the following detailed description of various embodiments in connection with the accompanying drawings, in which:

FIGS. 1-9, as a whole, illustrate sequential steps of an exemplary method for using the apparatus.

Figure 1:
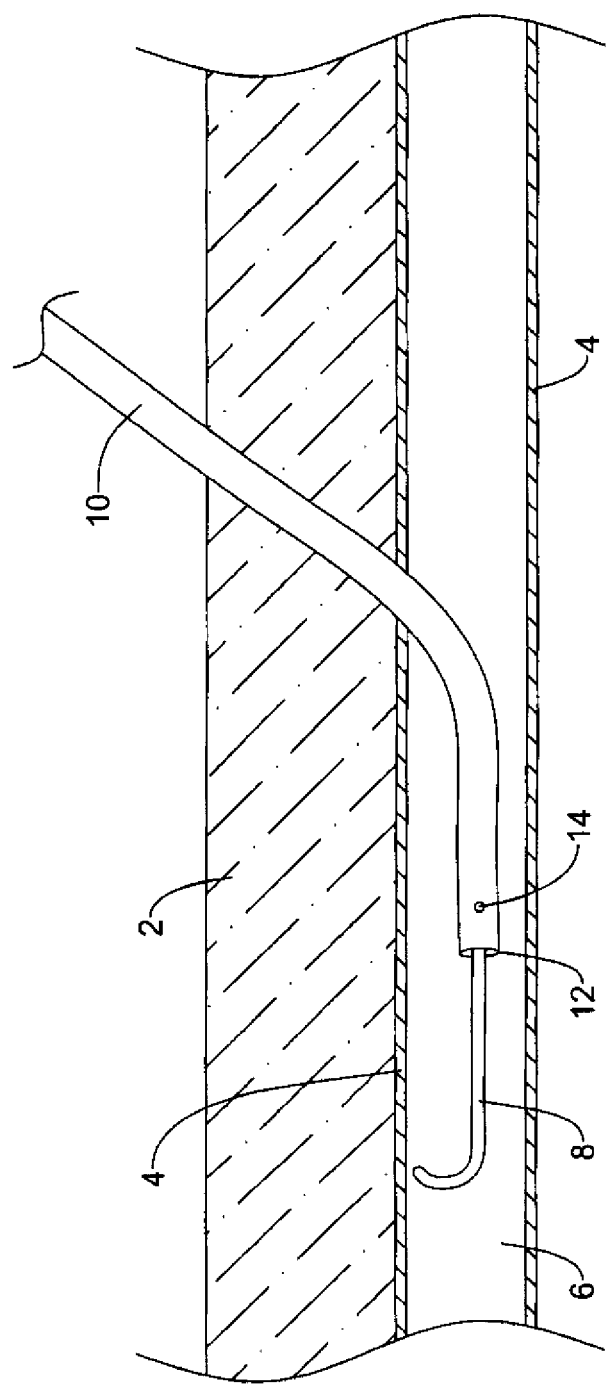
FIG. 1 is a side-view schematic drawing of an exemplary pinching apparatus for closing and/or sealing an opening in a blood vessel inserted into a blood vessel where the figure illustrates a particular step in a method of use.

While the embodiments described herein are amenable to various modifications and alternative forms, specifics thereof have been shown by way of example in the drawings and will be described in detail. It should be understood, however, that the intention is not to limit the devices and devices to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.718, 3, 3.14159265, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Both a device according to an embodiment of the present disclosure and a method according to an embodiment of the present disclosure may be readily understood with reference to FIGS. 1-9, which are side-view schematic drawings of a method of using an exemplary pinching device for closing and/or sealing an opening in a blood vessel.

As shown FIG. 1, a guidewire 8 may be inserted percutaneously through a body layer 2 and a vessel wall 4 into a lumen 6 of a vessel. It is contemplated that this guidewire 8 was introduced for one or more previous therapeutic interventions such as an angioplasty or stent procedure which has, at this point, already been performed. What remains to be done is to remove the guidewire 8 and seal the puncture through the vessel wall 4.

To this end an introducer sheath 10 having an open distal end 12 may be introduced over the guidewire 8 until the distal end 12 is within the blood vessel lumen 6. One way to ensure the introducer sheath 10 is properly positioned is to provide a bleed hole 14 fluidly connected to the lumen of the introducer sheath 10.

Figure 2:
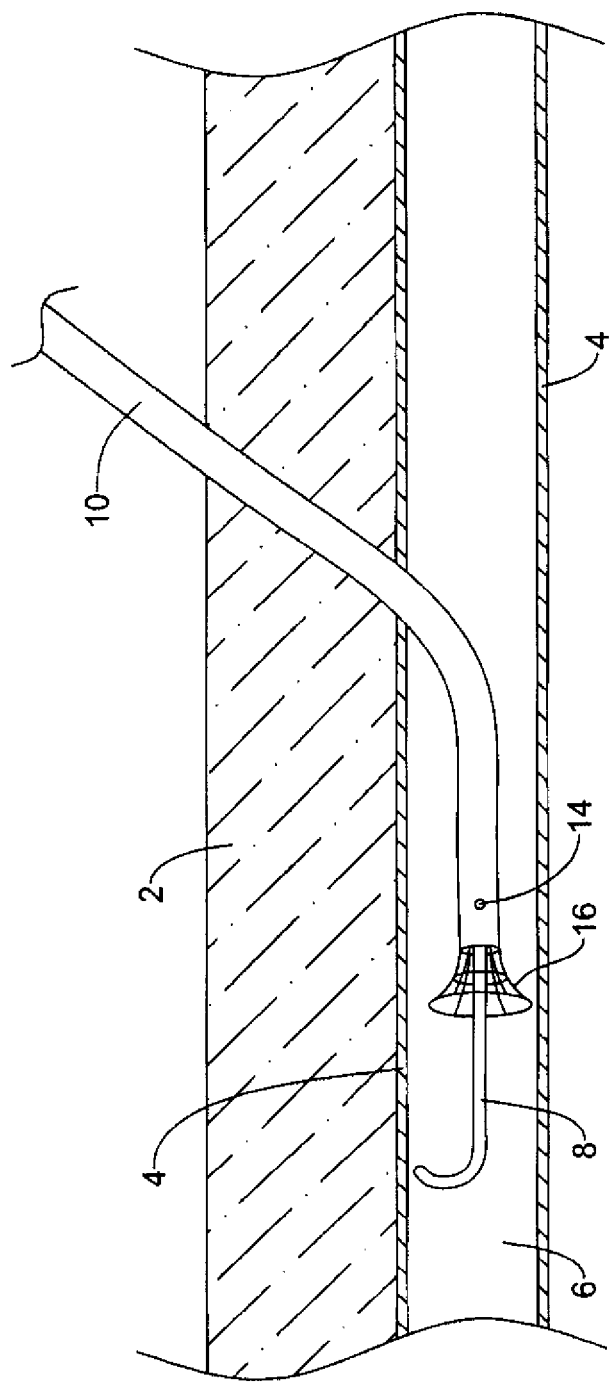
FIG. 2 is a side-view schematic drawing of the apparatus of FIG. 1 for closing and/or sealing an opening in a blood vessel inserted into a blood vessel where the figure illustrates a particular step in a method of use.

Turning to FIG. 2, when the introducer sheath 10 is positioned such that its distal end 12 is within the blood vessel lumen 6, an anchoring member 16 may be advanced through the introducer sheath 10. The anchoring member 16 can have an expandable distal end. In the configuration shown, the distal end of the anchoring member 16 can expand when unconstrained. Such an anchoring member may be made from resilient wires such as nitinol or stainless steel, where the wires are parallel to an elongate axis of the device. Such an anchoring member 16 may also be made from loosely woven wires or other suitable configuration that expands when unconstrained. Other configurations, where the anchoring member distal end expands in response to some positive actuation such as a pull wire or the introduction of an inflation fluid are also contemplated.

Figure 3:
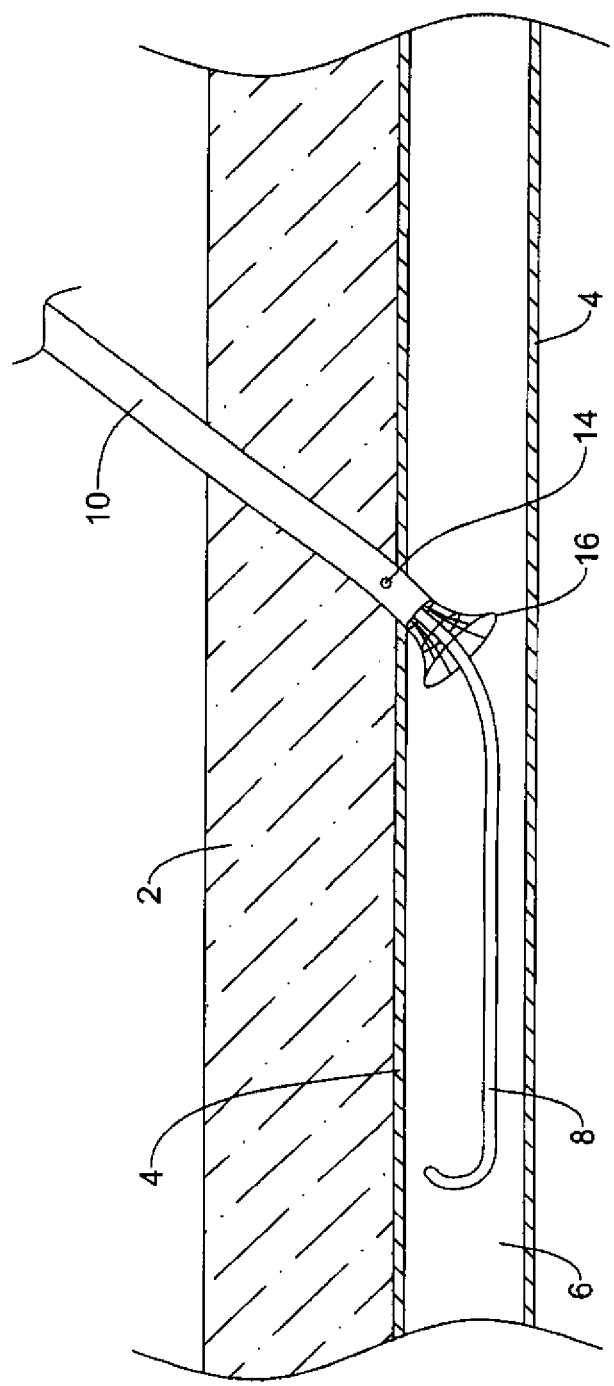
FIG. 3 is a side-view schematic drawing of the apparatus of FIG. 1 for closing and/or sealing an opening in a blood vessel inserted into a blood vessel where the figure illustrates a particular step in a method of use.

As shown in FIG. 3, when the distal end of the anchoring member 16 is expanded, both the introducer sheath 10 and anchoring member 16 are pulled proximally to seat the anchoring member 16 against the interior of the vessel wall 4. This action properly locates the distal end of the introducer sheath 10 at the vessel wall 4 for subsequent steps.

Figure 4:
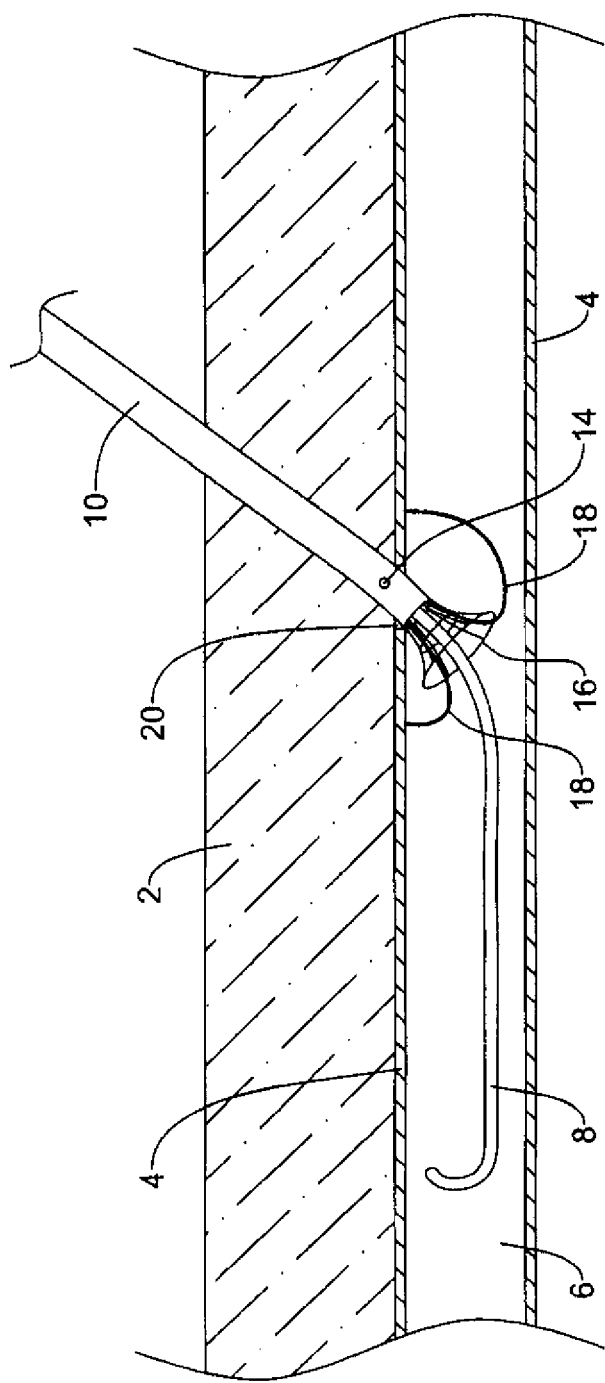
FIG. 4 is a side-view schematic drawing of the apparatus of FIG. 1 for closing and/or sealing an opening in a blood vessel inserted into a blood vessel where the figure illustrates a particular step in a method of use.

FIG. 4 illustrates a support member having a plurality of support legs 18 being advanced distally from inside the anchoring member 16. The support member has a plurality of support legs 18 that can be arranged cylindrically. There may be three, four, five, six, seven eight or another suitable number of support legs. The support legs 18 can be configured such that they bend away from the central longitudinal axis of the device. In some embodiments, the support legs 18 can curve such that they begin to point in a proximal direction. The distal ends of the support legs 18 can engage the interior of the vessel wall 4 to support the vessel wall 4 and hold it in place. Although only two support legs 18 are visible in the figures, it should be understood that the support legs 18 surround the opening 20 in the vessel wall 4.

Figure 5:
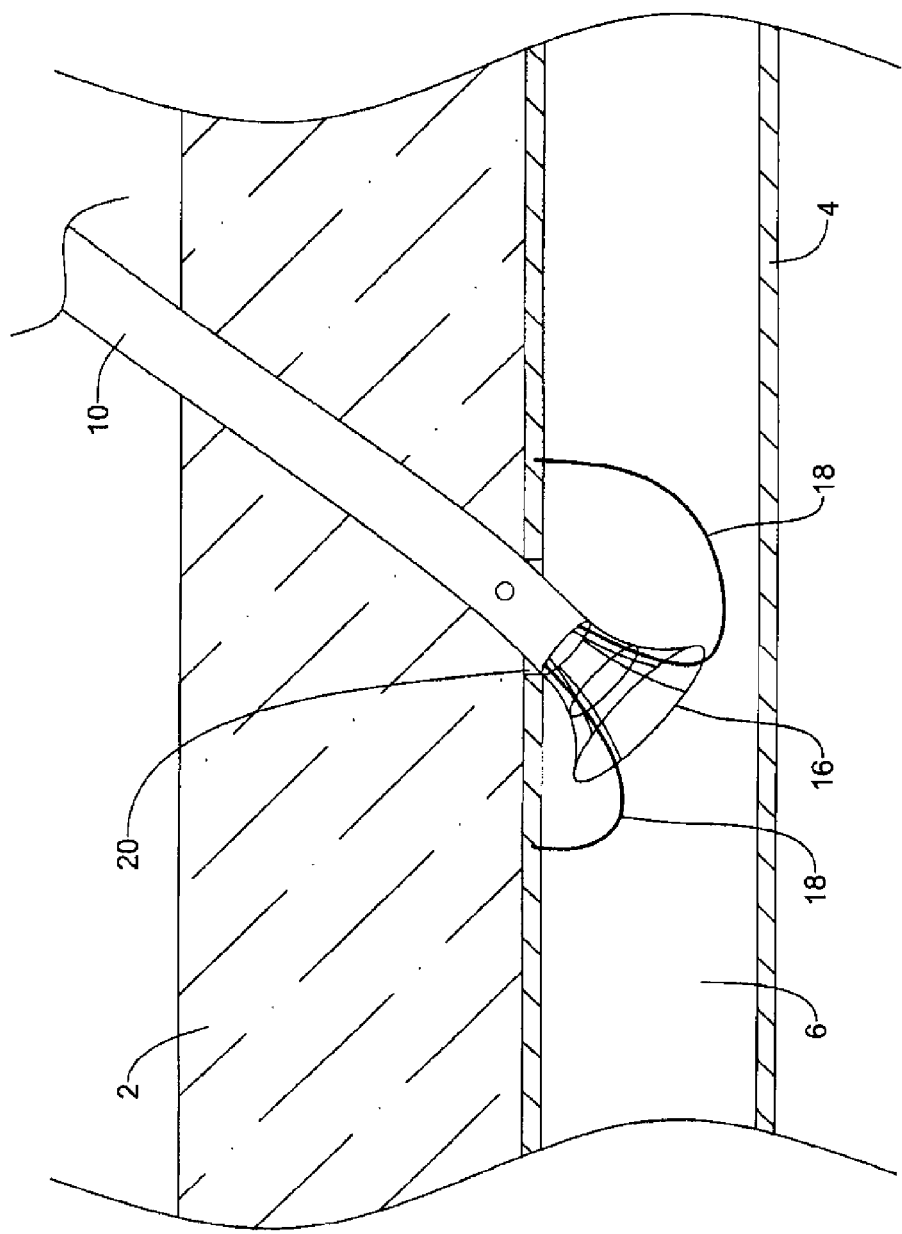
FIG. 5 is a side-view schematic drawing of the apparatus of FIG. 1 for closing and/or sealing an opening in a blood vessel inserted into a blood vessel where the figure illustrates a particular step in a method of use.

The guidewire 8 may be withdrawn at this point as illustrated in FIG. 5 or at another suitable time. For example, the guidewire may be withdrawn at other times prior to drawing the opening 20 in the vessel wall 4 closed.

Figure 6:
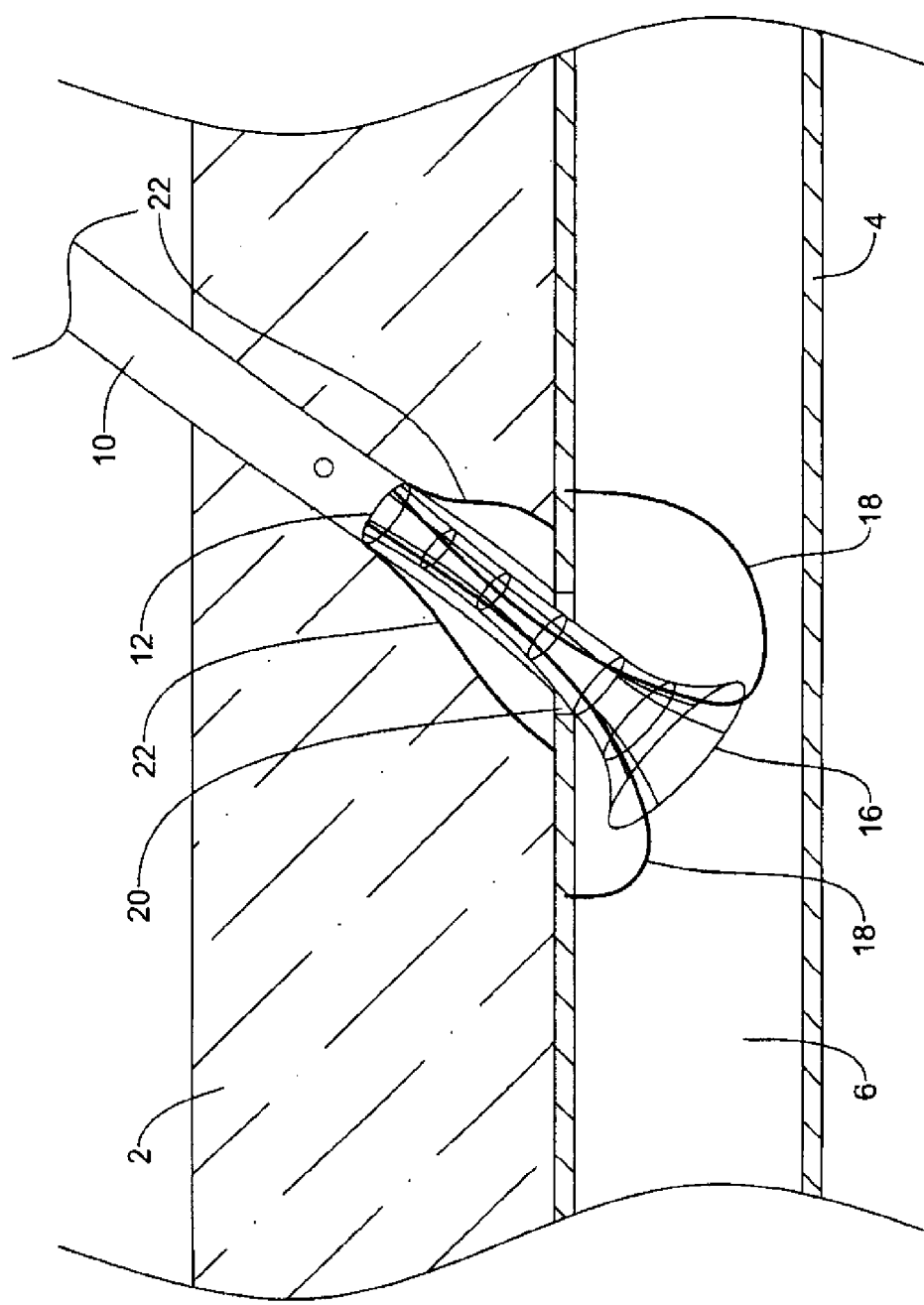
FIG. 6 is a side-view schematic drawing of the apparatus of FIG. 1 for closing and/or sealing an opening in a blood vessel inserted into a blood vessel where the figure illustrates a particular step in a method of use.

FIG. 6 illustrates a step where the pincher member is introduced. The pincher member can be located between the anchor member 16 and the introducer sheath 10. The pincher member includes a plurality of elongate pincher arms 22 that have free distal ends. The pincher arms 22 can be arranged in a cylinder about the anchor member 16. When unconstrained, the pincher arms 22 can expand radially away from the anchor member 16, as shown in FIG. 6. This action forces the substance of the body layer 2 away from the opening 20 in the vessel wall 4.

In some embodiments the method of deploying the pincher arms can include the following steps. The introducer sheath 10 may then be withdrawn proximally to allow the pincher arms 22 to expand as shown in FIG. 6. The pincher arms 22 may then be advanced distal to engage the vessel wall 4. The pincher arms may pierce the vessel wall 4 and may be provided with sharp distal ends for this purpose. Although only two pincher arms are visible in the figures, it should be understood that the pincher arms 22 surround the opening 20 in the vessel wall 4.

Figure 7:
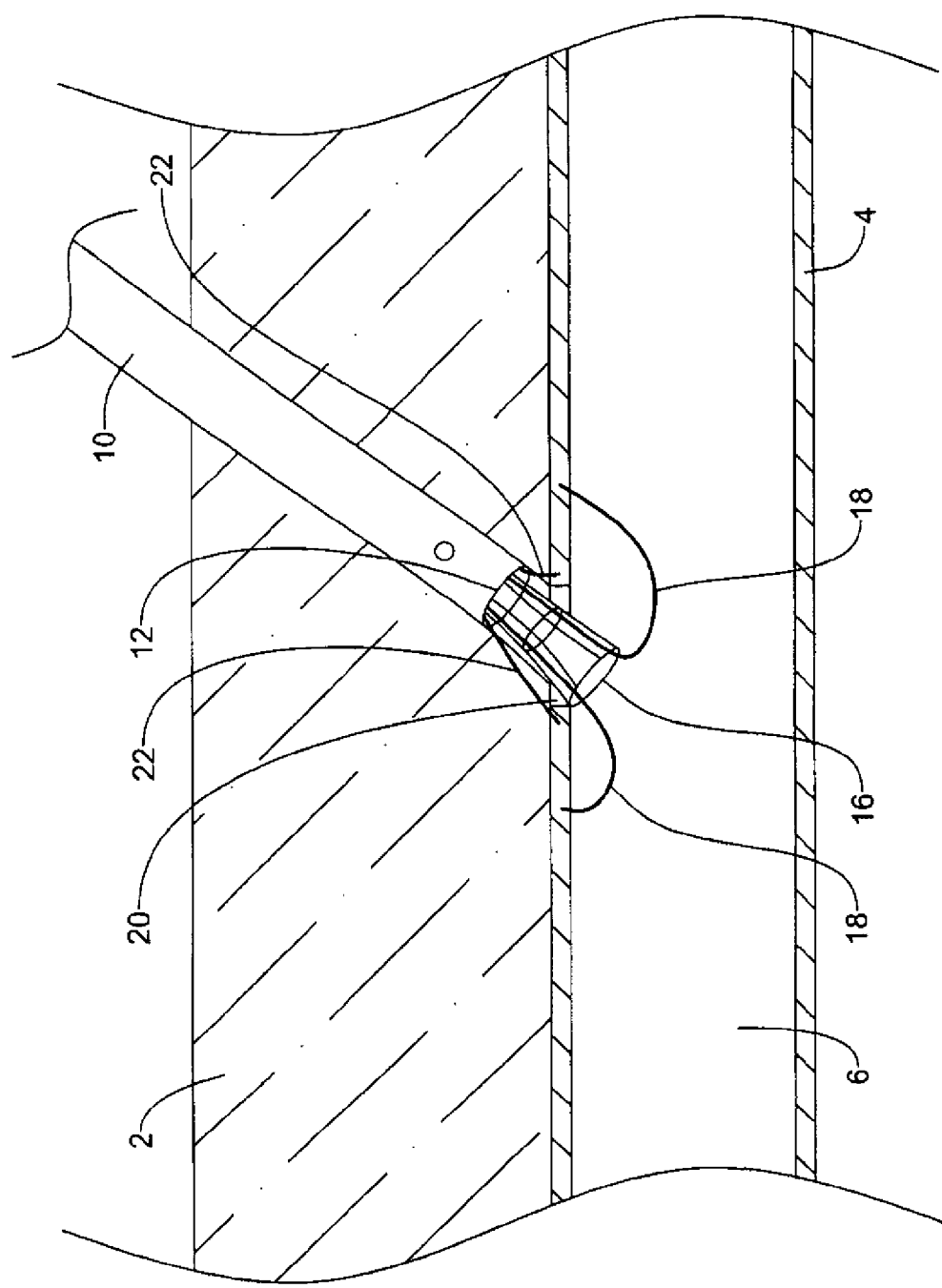
FIG. 7 is a side-view schematic drawing of the apparatus of FIG. 1 for closing and/or sealing an opening in a blood vessel inserted into a blood vessel where the figure illustrates a particular step in a method of use.
Figure 8:
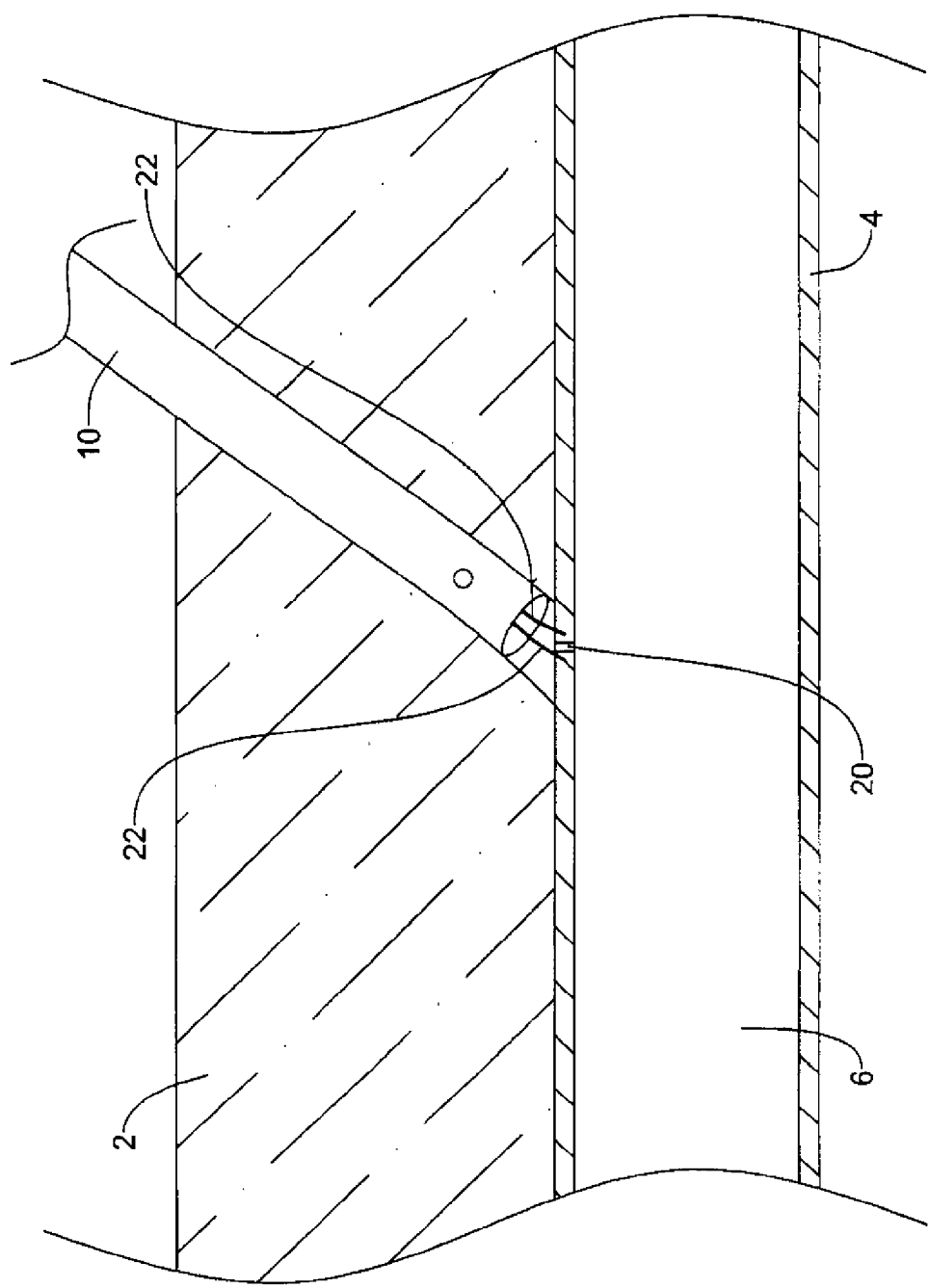
FIG. 8 is a side-view schematic drawing of the apparatus of FIG. 1 for closing and/or sealing an opening in a blood vessel inserted into a blood vessel where the figure illustrates a particular step in a method of use.

Once the pincher arms engage the vessel wall 4, the introducer sheath 10 (or another tubular member) may be advanced distally to push the pincher arms together again, as shown in FIG. 7. The anchor member 16 and support member support legs 18 may be withdrawn proximally. Because the distal ends of the pincher arms 22 were engaged with the vessel wall 4 before they were pushed together by the introducer sheath, the act of pushing the distal ends of the pincher arms together pinches the opening 20 closed, as shown in FIG. 8. At this point, the apparatus may be left in position for a sufficient period of time (dependent on the blood thinning regimen, if any) to allow clotting and cause full hemostasis. A sufficient period of time may be between five and ten minutes.

Figure 9:
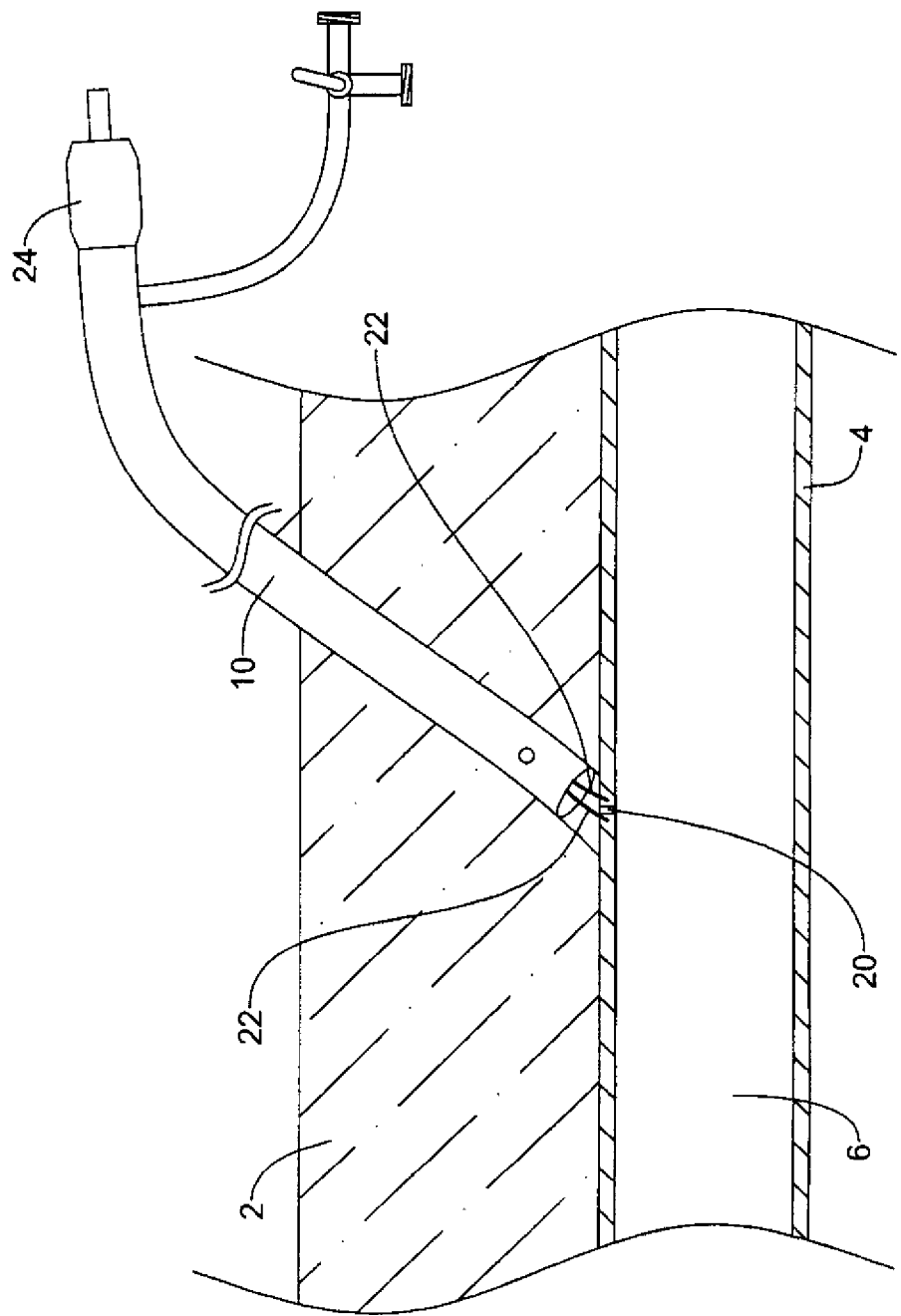
FIG. 9 is a side-view schematic drawing of the apparatus of FIG. 1 for closing and/or sealing an opening in a blood vessel inserted into a blood vessel where the figure illustrates a particular step in a method of use.

The full apparatus, shown in FIG. 9 with a hub 24, may be then be withdrawn from the body and the external opening through the body layer 2 may be closed with tape, a stitch or another suitable method.

In one method for pinching an opening 20 in a vessel wall 4 closed, the following elements may be introduced percutaneously into a blood vessel: a guidewire 8, an introducer sheath 10 that may have a distal end 12 and a bleed hole 14 near the distal end 12, and an anchoring mechanism 16 that has a distal end that expands when unconstrained. The introducer sheath 10 may be introduced over the guidewire and may be advanced until the bleed hole 14 is distal the vessel wall 4.

Next, the anchoring mechanism 16 may be advanced distally out through the distal end of the introducer sheath 10 until the distal end 12 of the anchoring mechanism 16 may be distal the distal end 12 of the introducer sheath 10. The distal end 12 can then expand in the blood vessel lumen. The introducer sheath 10 and anchoring mechanism 16 can then moved proximally until the expanded distal end of the anchoring mechanism 16 abuts the vessel wall 4. The distal end of the anchoring mechanism 16 may expand to create a proximally facing surface, and it is this proximally facing surface which may abut the vessel wall 4.

A pincher member may then be introduced through the introducer sheath. The pincher member may have at its distal end a plurality of elongate pincher arms 22, where each of the plurality of elongate pincher arms 22 have a free distal end such that when the pincher member distal end is unconstrained, the free distal ends of the elongate pincher arms 22 are biased to expand radially. The pincher member may then be moved distally such that the distal end of the pincher member is inside the introducer sheath 10 and proximate the vessel wall 4. Next, the introducer sheath may be retracted relative to the pincher member such that the plurality of elongate pincher arms distal ends expand radially. The pincher member may then be advanced distally to engage the distal ends of the elongate pincher arms 22 with the vessel wall 4. In some cases, the distal ends of the elongate pincher arms may pierce the vessel wall 4.

Once the elongate pincher arms 22 are engaged with the vessel wall, the introducer sheath 10 may be advanced over the pincher member to collapse the distal ends of the plurality of elongate pincher arms 22. This preferably causes the opening 20 in the vessel wall to either contract in size or to close.

With the elongate pincher arms 22 engaged with the vessel wall and collapsed by the introducer sheath 10, one waits a period of time. This period of time is preferably sufficient to permit clotting and may be, for example, between 5 and 10 minutes.

After the waiting, the anchoring mechanism 16, pincher member and introducer sheather 10 may be withdrawn proximally. The anchoring mechanism may be withdrawn prior to withdrawing the pincher member. In another variation, the anchoring mechanism or the anchoring mechanism and the guidewire may be withdrawn prior to waiting the period of time.

In a variation that may include most or all of the previous steps, the following further steps may also be included. An interior support member may be slidably disposed in the anchoring member, where the interior support member may have at its distal end a plurality of elongate support legs 18. Each of the plurality of elongate support legs 18 may have a free distal end such that when the distal end of the interior support member is unconstrained, the free distal ends of the plurality of elongate support legs 18 curve outwardly away from the longitudinal axis. This interior support member may be advanced distally out from the anchoring mechanism and then used to support the vessel wall 4. The distal ends of the elongate support legs 18 may pierce the vessel wall. These steps regarding the interior support member may be performed after the anchoring member may be moved to abut the vessel wall and prior to engaging the vessel wall with the elongate pincher arms. The support member may be withdrawn prior to withdrawn the pincher member or may be withdrawn prior to waiting the period of time.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A device for pinching an opening in a vessel wall, comprising:
    an introducer sheath having a proximal end, a distal end, a longitudinal axis extending therebetween, a lumen having an opening at the distal end and a bleed hole proximate the distal end;
    an anchoring member, the anchoring member having a tubular shape and an interior lumen having an opening at a distal end of the anchoring member, wherein the distal end of the anchoring member has a cylindrical shape in a first constrained state and a flared shape in a second unconstrained state, wherein the anchoring member is slidably disposed in the introducer sheath;
    a pincher member slidably disposed between the anchoring member and the introducer sheath, the pincher member having a proximal end and a distal end, the pincher member comprising at its distal end a plurality of elongate pincher arms configured to pierce the vessel wall, each of the plurality of elongate pincher arms having a free distal end such that when the pincher member distal end is unconstrained by the introducer sheath, the free distal ends of the elongate pincher arms are biased to expand radially away from the anchoring member; and
    an interior support member slidably disposed in the anchoring member, the interior support member having a proximal end and a distal end, the interior support member comprising at its distal end a plurality of elongate support legs, each of the plurality of elongate support legs having a free distal end such that when the distal end of the interior support member is unconstrained, the free distal ends of the plurality of elongate support legs curve outwardly away from the longitudinal axis.

2. The device of claim 1 wherein the anchoring member comprises a plurality of resilient wires.

3. The device of claim 2 wherein a plurality of the resilient wires extend parallel to the longitudinal axis when in the constrained state.

4. The device of claim 2, wherein the plurality of resilient wires are woven in a loose weave.

5. The device of claim 1 wherein the distal ends of the elongate pincher arms comprise a sharp distal point.

6. The device of claim 5 wherein when the distal end of the interior support member is unconstrained, the free distal ends of the plurality of elongate support legs point in a proximal direction.

7. A device for pinching an opening in a vessel wall, comprising:
    an introducer sheath; an anchoring member, the anchoring member having a tubular shape and an interior lumen having an opening at a distal end of the anchoring member, wherein the distal end of the anchoring member has a cylindrical shape in a first constrained state and a flared shape in a second unconstrained state, wherein the anchoring member is slidably disposed in the introducer sheath;
    a pincher member slidably disposed between the anchoring member and the introducer sheath, the pincher member having a proximal end and a distal end, the pincher member comprising at its distal end a plurality of elongate pincher arms configured to pierce the vessel wall, each of the plurality of elongate pincher arms having a free distal end such that when the pincher member distal end is unconstrained by the introducer sheath, the free distal ends of the elongate pincher arms are biased to expand radially away from the anchoring member; and
    an interior support member slidably disposed in the anchoring member, the interior support member having a proximal end and a distal end, the interior support member comprising at its distal end a plurality of elongate support legs.

8. The device of claim 7 wherein the distal ends of the elongate pincher arms comprise a sharp distal point.

9. The device of claim 7 wherein each of the plurality of elongate support legs having a free distal end such that when the distal end of the interior support member is unconstrained, the free distal ends of the plurality of elongate support legs curve outwardly away from the longitudinal axis.

* * * * *